United States Patent
Nemoto

(10) Patent No.: US 6,894,707 B2
(45) Date of Patent: May 17, 2005

(54) DISPLAY DEVICE FOR A MEDICAL TOMOGRAPHIC IMAGE

(75) Inventor: Shigeru Nemoto, Tokyo (JP)

(73) Assignee: Nemoto Kyorindo Co., Ltd., Tokyo (JP)

(*) Notice: Subject to any disclaimer, the term of this patent is extended or adjusted under 35 U.S.C. 154(b) by 556 days.

(21) Appl. No.: 09/788,650

(22) Filed: Feb. 21, 2001

(65) Prior Publication Data

US 2002/0054038 A1 May 9, 2002

(30) Foreign Application Priority Data

| Feb. 22, 2000 | (JP) | .............................. 2000-044524 |
| Sep. 20, 2000 | (JP) | .............................. 2000-285535 |
| Feb. 15, 2001 | (JP) | .............................. 2001-038522 |

(51) Int. Cl.[7] ............. G06F 3/14; G06F 19/00; A61B 6/03
(52) U.S. Cl. ............. 345/730; 345/732; 345/804; 345/184; 345/424; 600/425; 600/427
(58) Field of Search ............. 345/730, 732, 345/424, 473, 804, 833, 781, 702, 771, 784, 786, 788, 789, 866, 765, 961, 184, 156; 715/500.1, 517, 526; 600/407, 410, 411, 416, 425, 427

(56) References Cited

U.S. PATENT DOCUMENTS 6,734,880 B2 * 5/2004 Chang et al. ............. 345/730 X

* cited by examiner

*Primary Examiner*—Raymond J. Bayerl
(74) *Attorney, Agent, or Firm*—Oblon, Spivak, McClelland, Maier & Neustadt, P.C.

(57) ABSTRACT

The display device for tomographic image has a display, a hard disk, a mechanical slide-bar for setting a display speed for series of tomographic images and a controller. This device is used for displaying tomographic images in the manner of paging on the display for the series based on a speed set by the mechanical slide-bar.

7 Claims, 10 Drawing Sheets

(a)

(b)

(c)

DISPLAY DEVICE FOR A MEDICAL TOMOGRAPHIC IMAGE

BACKGROUND OF THE INVENTION (i) Field of the Invention

This invention relates to a display device for displaying a tomographic image used for diagnosis and to a displaying process.

(ii) Description of the Prior Art

For diagnosis using a two-dimensional medical image such as an x-ray CT (computed tomography) image, an MRI, an angioimage and angiographic image, a film viewer using a backlight called a Schaukasten has been used after printing the image on a film.

In X-ray CT, a helical CT device has been frequently used, where a patient is helically scanned for collecting data while continuously rotating an X-ray light and moving the patient on a platform in a given rate. More recently, a helical scanning procedure has been using a multi-slice CT device where a plurality of detectors are aligned to simultaneously collect data for multiple slices during one rotation.

Such advance in technology has achieved extension of a scanning range, reduction in a testing time and improvement in resolution along a body axis. For example, a CT image with a 0.5 mm pitch has been able to be obtained in multi-slice CT and thus 900 pieces of CT images can be obtained in a short time when scanning 45 cm of a body. However, it has led to an enormous amount of data, taking a considerably long time for reading each image using a Schaukasten and resulting in a huge number of films. For reducing the number of films, there has been an attempt that the number of cuts (i.e., slice images ) printed on one film (size: 35×43 cm) is increased to about 20 images. It, however, leads to reduction in size for one image , causing it difficult to read the image. There is, therefore, a limit in reduction in the number of films.

In addition, display devices for a CT image are known, in which many CT images can be displayed on a display such as a CRT using a computer not only as a 2D (two-dimensional) image but also as a 3D (three-dimensional) image. Some of these display devices have pager function that each of a plurality of CT images (hereinafter, a "CT image" refers to, unless otherwise indicated, a 2D image.) is displayed one slice by one slice in the manner of paging by manual or automatical operation. It has an advantage that more CT images can be compactly read compared with "Schaukasten", because it can eliminate the need for handling many films.

A device displaying a 2D or 3D image is manufactured and marketed by multiple manufactures. These devices are mainly operated by keyboard input and selection/operation in a display device using a mouse because the system utilizes a fixed hardware (a family such as MAC and DOS/V) for the purpose of universality in a software. To date, a variety of softwares allows us to display a 2D image, 3D image or a plurality of images by dividing a screen.

However, when an operator is intensely reading images on a screen by actually using such a universal system, it gives much stress to the operator to do key input from a keyboard or to select an event by clicking an icon indicated on a screen using a mouse. This is because operator's viewing points disperses two or more points. If a display device is used only as a viewer having pager function which shows in the manner of paging CT images (two-dimensional images), a computer compliant to 3D image displaying function may be of overspecification as a hardware, leading to a higher cost.

Thus, when a very technical operation such as reading a CT image (i.e., observing images for medical examination) is required, that is, when the results are very important and it is also needed to acquire the results as readily as possible, a universal system utilizing software is rather inferior in operability and may interfere concentration of the operator for intense image-reading.

In terms of softwares in a conventional display device for a CT image, there are display devices which can display a series of CT images in the manner of paging or display two or more static images, but there are no display devices which can display two series of CT images simultaneously in the manner of paging and there are no software dealing with such operation.

SUMMARY OF THE INVENTION

An objective of this invention for solving the problems is to provide a display device for a tomographic image which is convenient and of good operability for diplayinn a tomographic image in the manner of paging.

Another objective of this invention is to provide a display device which can display at least two series of tomographic images in the manner of paging and by which reliable diagnosis can be performed.

The first aspect of this invention provides a display device for tomographic image, comprising: (a) a display portion for displaying at least one series of tomographic images, (b) a storage mechanism for storing at least one series of tomographic image data, (c) a display-speed setting mechanism for setting a display speed for at least one series of tomographic images, and (d) a controller which receives data from the storage mechanism for the series and displays tomographic images in the manner of paging on the display portion for the series based on a speed set by the display-speed setting mechanism; the display-speed setting mechanism being a mechanical variable knob in a separate case from that comprising the controller.

The mechanical variable knob is preferably a mechanical slide-bar type variable adjuster.

The second aspect of this invention provides a display device for tomographic image, comprising: (a) a display portion for displaying at least two series of tomographic images, (b) a storage mechanism for storing at least two series of tomographic image data, (c) a display-speed setting mechanism for setting a display speed of each series for at least two series of tomographic images, and (d) a controller which receives data from the storage mechanism for each series and simultaneously displaying a plurality of series of tomographic images on the display portion for individual series based on a speed set by the display-speed setting mechanism.

It is preferable that the display device further comprises a synchronization command sending mechanism which matches display speeds for at least two series of tomographic images; whereby, the controller displays tomographic images in the manner of paging while synchronizing display speeds for a plurality series of tomographic images based on a synchronization command from the synchronization command sending mechanism.

The third aspect of this invention uses a mechanical variable adjusting knob as the display-speed setting mechanism in a separate case from that comprising the controller in the above second aspect. Herein, a mechanical slide-bar type of variable adjuster is particularly preferable.

The fourth aspect of the this invention provides a recording medium on which a program is recorded for displaying tomographic images on a display by a computer for the practice of the second and third aspects of the present invention. This program is adapted to execute the steps comprising: receiving data for at least two series of tomographic images from the storage mechanism, receiving a set of values for display speed for each series of tomographic images, and displaying a plurality series of tomographic images on a display simultaneously by displaying tomographic images in the manner of paging for each series.

Furthermore, the program is preferably a program for displaying tomographic images by synchronizing a display speed for a plurality series of tomographic images based on a synchronization command which matches a display speed for at least two series of tomographic images.

DETAILED DESCRIPTION OF THE INVENTION

Figure 1:
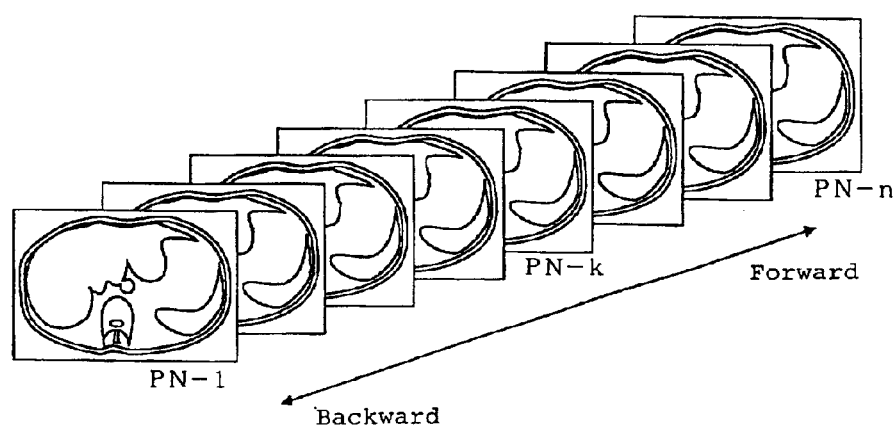
FIG. 1 schematically shows one series of tomographic images.

In the present invention, a series of tomographic images is a set of multiple tomographic images obtained by taking images under particular conditions for one patient. These include, as illustrated in FIG. 1, n pieces of images from image PN-1 to image PN-n where a given image PN-k and image PN-(k+1) is separated by a predetermined pitch (distance). The pitch is determined by the value calculated by (scan distance)/(image number) if any distance between images is constant. A display speed for images is a speed for forward-turning, i.e., forward-paging (or backward-turning, i.e., backward-paging) tomographic images, which may be given in, for example, the number of images turned over in a second.

Data for a series of tomographic images may comprise data about, for example, a pitch, an image position and imaging conditions.

The display device for a tomographic image according to the first aspect of this invention is a device which can display at least one series of tomographic images one by one in the manner of paging and uses a mechanical variable adjusting knob in a separate case (hereinafter, referred to as an "operation panel") from a display (display portion) or a computer. It can set a display speed without using key-input by a key board or click or drag using a mouse. Such a mechanical variable adjusting knob allows a user to easily and intuitively change a speed to a proper value in hand while gazing tomographic images displayed in turn on a display without averting his/her eyes.

Examples of a variable adjusting knob include a mechanical slide-bar type variable adjuster as later described in Examples and a rotating knob. The slide-bar type is preferable because an operator can forward-page or backward-page images on the basis of zero point and thus it is quite intuitive.

In the first aspect, it is operationally preferable that the operation panel comprises a start and/or a stop keys. With a start and a stop keys, an operator can move forward (or backward) to a given image and then start forward-turning (or back-turning) using a start key or can stop at an image important for diagnosis to carefully examine the tomographic image.

The display device for a tomographic image according to the second invention can simultaneously display at least two series of tomographic images on a display (display portion) and can display the tomographic images in the manner of paging at a display speed set for each series.

Figure 2:
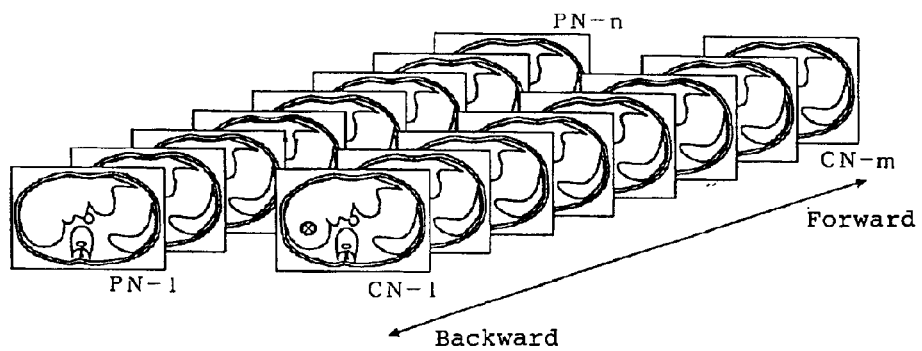
FIG. 2 schematically shows two series of tomographic images.

FIG. 2 schematically shows two series of tomographic images, which are different series mutually related for comparison. For example, the tomographic images in the first series (PN-1 to PN-n) are X-ray CT images under normal conditions while the tomographic images in the second series (CN-1 to CN-m) are X-ray contrasted CT image using a contrast medium for the same patient after injecting a contrast medium. Then, the images can be displayed in the manner of paging, comparing the simple CTs and the contrasted CTs.

In this case, the first and the second series can be synchronized, i.e., two series of tomographic images can be displayed at the same display speed, to provide different information for the same part in the body, resulting in more exact diagnosis. Such a display device for a tomographic image displaying at least two series of tomographic images in the manner of paging on the same display is unknown in the prior art. It is considerably effective because it can conveniently display the same part by synchronizing a plurality of series.

Different series to be compared with for medical examination may be classified, taking X-ray CT as an example, in terms of (a) use of a contrast medium: simple X-ray CT without a contrast medium and contrasted CT with contrast medium or (b) an imaging time: the latest CT images and previous images (in this case, a plurality series of the data obtained for the different time may be compared.). FIG. 2 shows the latest imaging series of simple X-ray CTs and a latest imaging series of contrasted CTs, but the latest imaging series of simple X-ray CTs can be compared with a previous imaging series of simple X-ray CTs. Rather than comparison between two series, more than two series may be compared; for example, four series can be compared in a combination of simple CT-latest, contrasted CT-latest, simple CT-previous and contrasted CT-previous, or for images at different times (e.g., simple CTs-latest, previous 1, previous 2 and previous 3).

In synchronizing series in the embodiment in FIG. 2, when these two series have the same pitch and the same number of images (m=n), an image number is the same, so that the images may be readily displayed by determining an image number as starting point and paging both two series of images at a given speed using a computer (controller). The image at a starting point for each series can be manually selected while looking at an image on a display. Here, it is quite convenient to use means for applying a mark on a displayed image for confirming the staring point.

Furthermore, for example, when a pitch or the number of images are different between series, synchronized display where positions of all images are completely matched is impossible. However, an operation program can be executed by controller such that a sub-series image closest to a main-series image is displayed in the light of a pitch or the number of images of the sub-series to the main series or sometimes an image is interpolated.

There are no restrictions to the format of tomographic image data stored in a storage mechanism in this invention. The data can be stored for each tomographic image or as data before reconstruction of each tomographic image such as raw data obtained by helical scanning. An example of a format for each tomographic image is a data format style in conformity with the DICOM specification which has become a standard format style for a CT image. Any suitable format such as JPEG and BMP (bitmap) may be used. In any format, it is required to store data for mutual relationship between individual image data such as data for the measuring conditions (or storing conditions of the images) including an image pitch and a measurement distance. In the second aspect of this invention, when synchronizing and displaying two or more series of tomographic images, the two or more series of tomographic images can be easily synchronized on the basis of the measurement conditions for each series. For a data format which does not store the data as data for each image, two or more series of tomographic images can be synchronized while reconstituting tomographic images for a required part in the light of measurement conditions (or storing conditions of the images).

In the second aspect of this invention, an operation for setting a display speed and commanding synchronization can be conducted by key-input with a universal keyboard or input by click or drag with a mouse using GUI on a display as interface. Thus in an embodiment of the second aspect of the present invention, a display-speed setting mechanism and/or a synchronization command sending mechanism may be a universal keyboard or a mouse cooperatively worked with soft ware which executes such functions. Using such a universal keyboard or mouse has an advantage that there are no particular restrictions to the number of series simultaneously displayed, but as described above, there still remains the problem of much stress to an operator in doing key input from a keyboard or in selecting an event by clicking an icon indicated on a screen using a mouse while intensely inspecting images on a screen.

Thus, the third aspect of this invention uses a mechanical variable adjusting knob in a separate case from that accommodating a display (display portion) and a computer body (controller) for setting a display speed in the above second aspect. Such mechanical variable adjusting knob is described in the first aspect of the present invention.

In the third aspect of this invention, the number of mechanical variable adjusting knobs in the operation panel may be appropriately changed in accordance with the purpose of embodiments of the invention. In an embodiment, the number of variable adjusting knobs are the same as the number of series so as to appropriately change paging speed for each series independently. Further, when displaying multiple series in a synchronized style, it is possible that a particular variable adjusting knob such as a variable adjusting knob controlling a main series can control a paging speed in synchronized display. In some cases, a variable adjusting knob exclusively for synchronized display may be provided. Alternatively, the number of mechanical variable adjusting knobs may be less than that of series. Thus, for example, a switching button (any kind of switch can be used) may be used to select a series. Therefore, only one variable adjusting knob may be used.

The most preferable style of a mechanical variable adjusting knob is a slide-bar style.

It is preferable that a key for commanding synchronization and, if a marker function is used, a key for commanding marking are mounted on an operation panel. As described in the first aspect, it is operationally preferable that a start and/or a stop keys are mounted on the operation panel.

In the third aspect of this invention, it is rather troublesome to simultaneously operate an excessive number of series of tomographic images. Thus, the number of the mechanical variable adjusting knobs mounted on the operation panel is usually 1 to 8, preferably 1 to 6, more preferably 1 to 4.

Preferably, an image displaying device for a tomographic image according to this invention (the first, the second and the third aspects) further comprises matrix displaying function whereby selected multiple images can be simultaneously displayed on a display. With the displaying function, for example, images for different parts in the same series can be aligned on the same screen. The aligned images may be selected with marking function or serial multiple images may be automatically aligned. The number of images displayed as a matrix may be changed depending on a size of a display used and a resolution. For example, the images are preferably displayed in 2×2 (4 pieces) or 4×4 (16 pieces). In the second and the third aspects of this invention, it is preferable that display for multiple series and matrix display for the same series can be switched. In the first and the third aspects of this invention, a switch for switching turning display between matrix display can be mounted together with a mechanical variable adjusting knob in a separate case.

In this invention (the first, the second and the third aspects), examples of the storage mechanism include devices integrated in a computer or disposed near a computer such as a hard disk, a flexible disk, a CD-ROM and a RAM. The storage mechanism also includes relatively wide category such as a communication system which can receive data from a network. Thus, all data required may not be simultaneously stored in the storage mechanism.

This invention will be more specifically described with reference to embodiments. The embodiments are related to the third aspect of this invention, but a skilled person in the art can readily understand the first and the second aspects by referring the following description.

<Embodiment 1>

Figure 3:
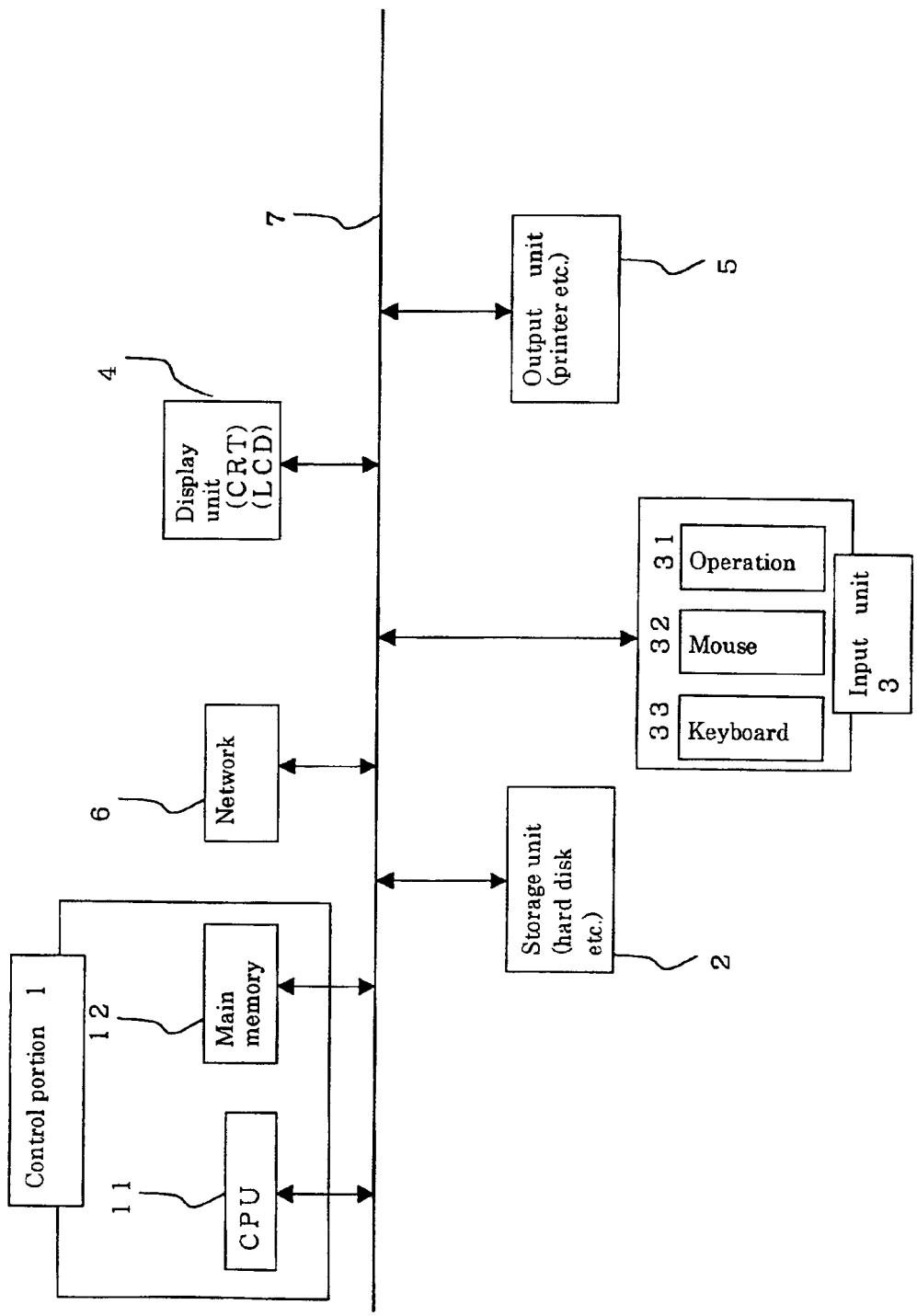
FIG. 3 is a block diagram illustrating a system configuration of Embodiment 1.

FIG. 3 is a block diagram schematically illustrating a system configuration of the first embodiment of this invention, where a controller portion 1 is equipped with, for example, a CPU 11 and a main memory 12; the CPU executes a program in cooperation with the main memory and controls a storage unit 2, a display unit 4, an input unit 3, an output unit 5 and a network 6, which are all connected to a system bus 7. The system bus 7 is a bus for transferring, e.g., image data. The storage 2 stores a plurality series of tomographic images and display series selected by the input unit 3 on the display unit 4. Herein, the network 6 may be the storage mechanism as described above.

The display unit 4 can display a tomographic image, and may also display, for example, a selection screen for selecting images to be displayed or patient data. The device used is preferably an LCD (Liquid Crystal Display) or CRT compliant to a high resolution image.

The input unit 3 comprises an operation unit 31, a mouse 32 and a keyboard 33. Preferably, operation procedure for inspecting images is exclusively conducted by the operation unit 31, and the mouse and the keyboard may be useful in operation before and/or after additional data input or reading (i.e. inspecting) an image.

Figure 4:
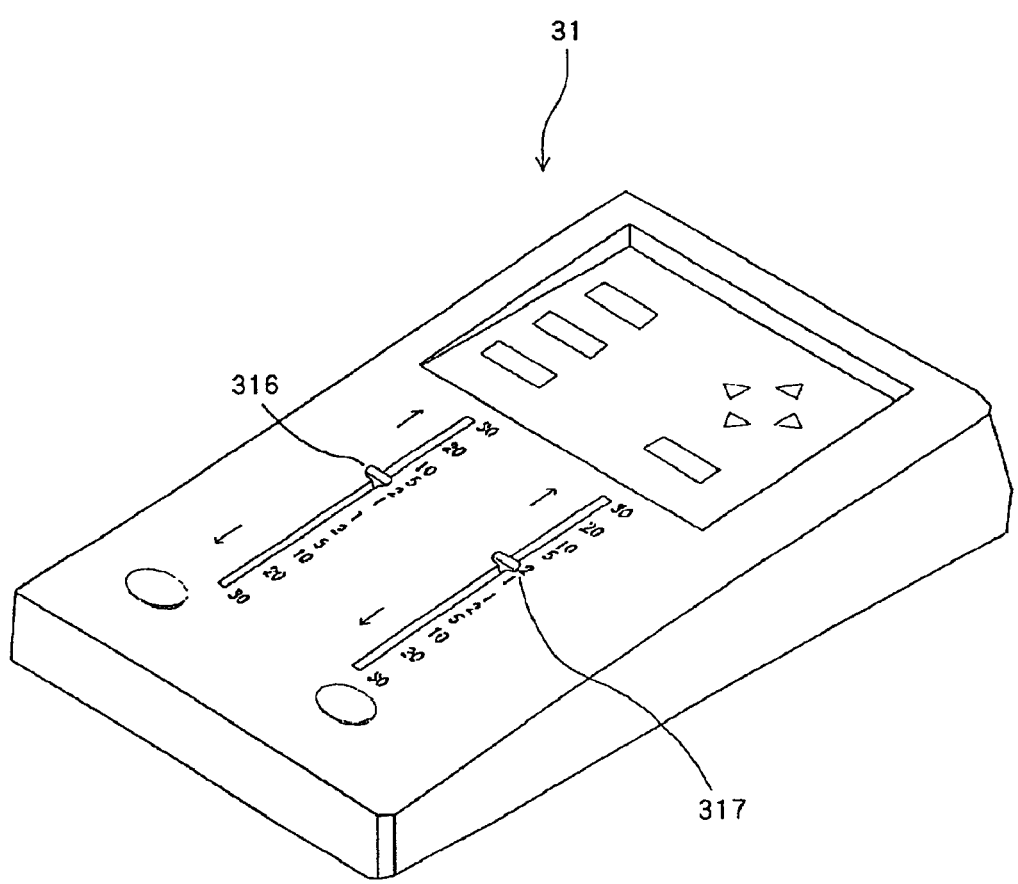
FIG. 4 illustrates an example of an operation unit.
Figure 5:
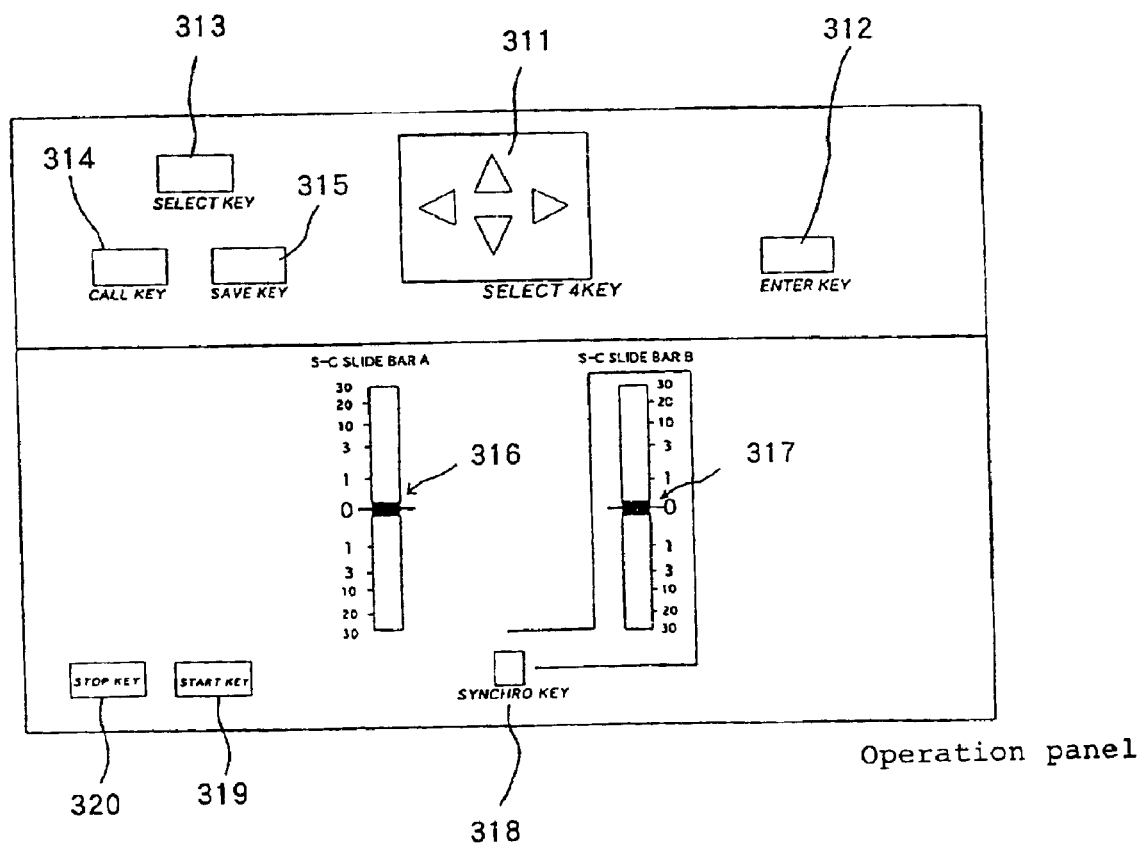
FIG. 5 illustrates an example of an operation panel in an operation unit.

FIG. 4 shows an example of the operation unit 31, which is in a separate case from that comprising a controller portion. FIG. 5 shows an operation panel in the operation unit 31. In the upper portion of the operation panel there is mounted a selection operation unit comprising matrix 4 keys 311 for selecting various items such as a displayed screen and required data including a patient's name, a decision key 312 for deciding selection alternatives, a selection key 313 selecting an item, a call key 314 for displaying a tomographic image constructed on the basis of the recording conditions and a recording key 315 giving a command for recording the present conditions. On the other hand, in the lower portion of the operation panel, there are mounted mechanical slide-bars 316, 317, a synchronization key 318 for displaying after synchronizing a display speed for each series for two series to be compared, a start key 319 for starting turning (paging forward or backward) and a stop key 320 for stopping turning (paging forward or backward) of tomographic images.

The operation unit is connected to the system bus 7 via a wired or infrared communication and the like. An image is displayed in the manner of paging on the basis of a signal from the operation unit.

The output unit 5 may be a usual printer (monochrome or color). Alternatively, it may have optionally a configuration which can output data to a laser imager for the convenience of the inspection of images using a Schaukasten.

An example of display will be described using the above device with reference to an exemplary operation procedure.

(1) Selection Between a Single Screen and Two Screens for Comparison:

In this example, after starting up a display device for a tomographic image, a screen for selecting a single screen or two screens for comparison is displayed. When selecting two screens for comparison, it is selected using, for example, matrix keys 311 or a decision key 312.

(2) Selection of an Image Series:

Matrix keys 311 or a decision key 312 is used for selecting a series displayed in each of the left and the right split screens.

For example, image series to be displayed in the right and the left screens are selected from the indicated list in the screen. Specifically, vertical and horizontal keys in the matrix 4 keys 311 are used to select an image series displayed in the right screen. After selection, the decision key is pressed for confirmation. Vertical and horizontal keys are used to select an image series displayed in the left screen. After selection, the decision key is pressed for confirmation.

Figure 6:
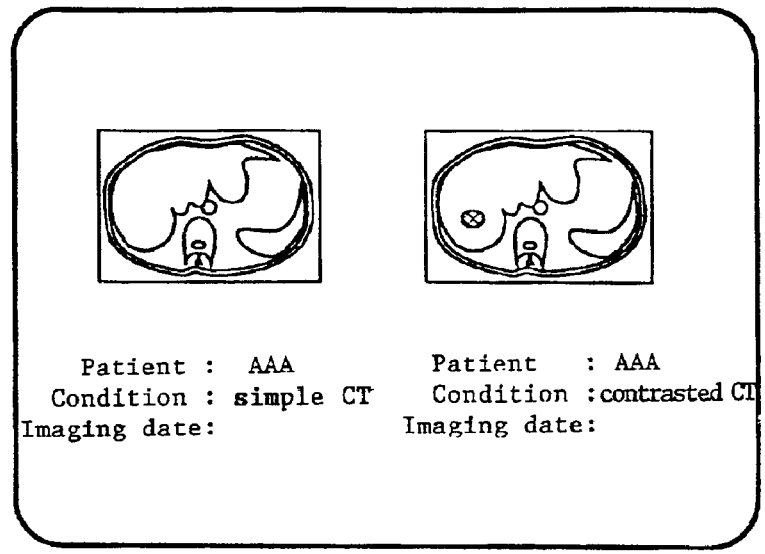
FIG. 6 shows display of two screens for comparison in paging-display.
Figure 7:
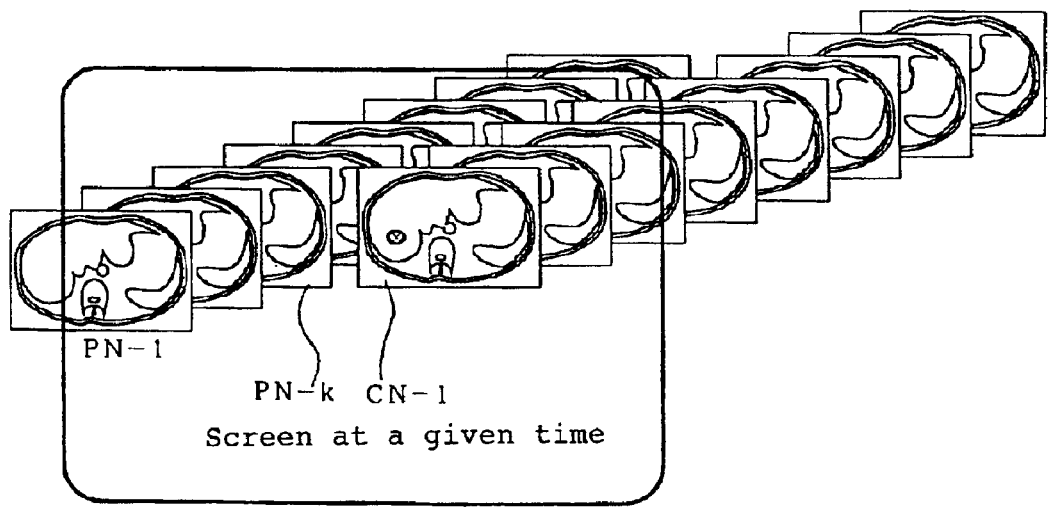
FIG. 7 schematically shows paging of the left series of images.

(3) Displaying Images in The Manner of Paging:

Thus, a screen as shown in FIG. 6 appears on the display. Then, a slide bar for setting an image display speed is operated. The slide bar in the operation unit where an image display speed can be changed can be operated to appropriately set a speed for displaying the selected image series. In FIG. 5, the tomographic images in the left screen are turned forward by sliding upward (far side in FIG. 4) the slide bar 316 as schematically shown in FIG. 7. The tomographic images in the left screen are turned backward by sliding downward (near side in FIG. 4) the slide bar. The slide bar 317 similarly defines paging of the tomographic images in the right screen.

The numbers by the side of the slide bar indicate a paging speed. In this example, they indicate the number of images per 1 sec. (pieces/sec). Alternatively the unit may be a feeding pitch per 1 sec. (mm/sec). It is not necessary to set the moving distance of the slide bar linearly to the paging speed. In this example, a speed can be finely set within ±¼ from the center while images are turned at a 10-fold speed over ±¼ from the center. In the latter case, since display is considerably rough, display can be conducted omitting the images at a rate of one per three or two per five.

The slide bar stays at an appropriate set position and the display screen may be changed in real time depending on moving of the bar. The slide bar may be moved continuously or in a multistep style where the bar stays at a particular position with tactile feeling. It is preferable that for zero point, tactile feeling is given for clearly indicating the position.

A combination of the start key 319 and the stop key 320 can be used to more conveniently conduct the operation of feeding images in a given speed or stopping. The start key 319 may be assigned, for example, a function of paging images one by one or restarting after stopping image paging with the stop key. The stop key may be pressed to stop the screen at a required image (displaying a given required image) for scrutinizing the tomographic image.

(4) Displaying in the Manner of Paging two Image Series for Comparison in a Synchronized Style:

A synchronization key 318 is operated for displaying the right and the left images in the screen in a synchronized style. In this example, only the right slide bar 317 is active when operating the key. By operating the slide bar, the right and the left images are simultaneously paged (forward or backward).

In an actual exemplary operation, the right and the left images are separately operated to determine a start point. At the point, the synchronization key is pressed to enter a synchronization state. In this case, if marking function is provided, it is convenient for determining the start point.

(5) Other Functions:

A calling key and a recording key are those related to calling and recording of conditions and environment for display, respectively. When conducting display under particular conditions, the conditions can be recorded and next time, the conditions may be called to easily conduct display under the same conditions without again setting conditions.

There may be added as an option a function related to image quality or image expression such as enlargement/ reduction or shifting of a screen and CT values. In such a case, a key executing such a function may be mounted in the operation unit or an appropriate combination of selection keys or matrix 4 keys may be used to give a command for such a function.

<Embodiment 2>

As a second embodiment, there will be described a display device for a tomographic image which can simultaneously display four images in the manner of paging. The general configuration of the device is as described in Embodiment 2.

Figure 8:
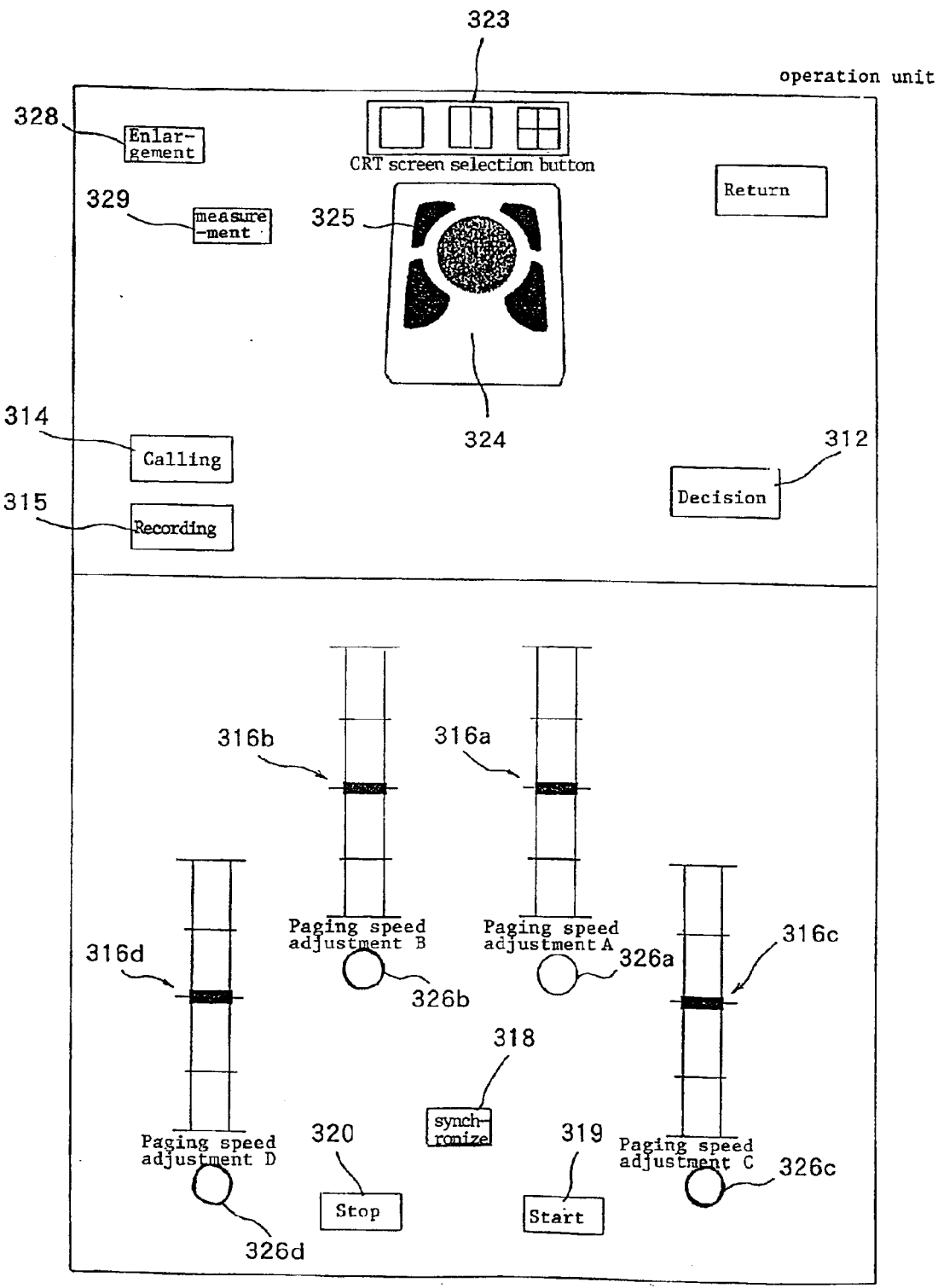
FIG. 8 shows an operation panel in Embodiment 2.

The device of this embodiment comprises an operation unit as shown in FIG. 4, on which keys, a track ball and a slide bar as shown in FIG. 8 are mounted.

Figure 9:
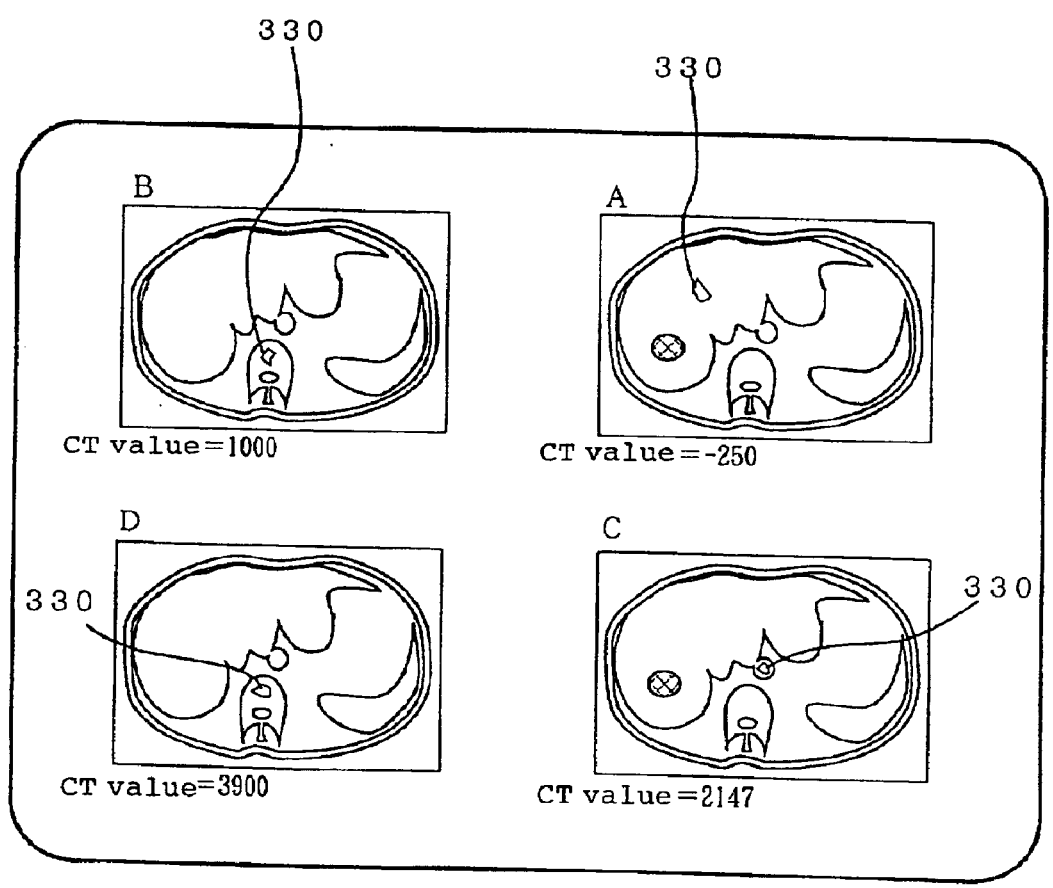
FIG. 9 shows display of four screens.

FIG. 9 shows a display where four images are displayed. Various combinations of four images are possible; for example, 4 screens/4 series, 4 screens/1 series or 4 screens/2 series. Four screens/4 series display is that displays different series allocated to individual split screens; for example, screen A: contrasted CT image (latest), screen B: simple CT image (latest), C: contrasted CT image (previous), screen D: simple CT image (previous); and 4 screens are used for displaying in the manner of paging. Four screens/1 series display is that displaying, for example, a series of contrasted CT tomographic images (latest) using four split screens where, for example, screen A may display paging images while screens B, C and D may display static images. Four screens/2 series display is that where, for example, screen A: contrasted CT image (latest) is compared with screen B: simple CT image (latest) and screens C and D are used for displaying these static images. Alternatively screen A: contrasted CT image (latest) and screen B: simple CT image (latest) may be compared while being displayed in the manner of paging and screens C and D may display their enlarged or reduced images in the manner of paging.

An example of display will be described using the above device with reference to an exemplary operation procedure.

(1) Selection of the Number of Screens:

As shown in FIG. 8, this device comprises screen selection keys 323 and one of three keys may be pressed to select single-screen, two-screen or four-screen display. Here, four-screen display is selected.

(2) Selection Of Images Allocated To Split Screens:

Images displayed in each quadrant screen are selected as described in Embodiment 1, using a track ball 324 and buttons 325 disposed around the ball.

(3) Paging of Images:

After selecting, for example, a series to be displayed in each screen, quadrant screens appear on a display as shown in FIG. 9. Then, slide bars for setting an image display speed 316a to 316d are operated to appropriately set a speed for displaying an image series. The track ball and the buttons may be used to determine which split screen becomes active. It can be set that an image may not be paged even by pressing a start key when the slide bar is at 0 point.

(4) Synchronized Paging of Images for Comparison:

For displaying images on the screens in synchronized manner, a synchronization key 318 is used as described in Embodiment 1. A starting point of paging may be set using a slide bar allocated to each screen as described in Embodiment 1. Alternatively, it may be set using a track ball.

The device of this embodiment comprises marker keys 326a to 326d, whereby a starting image may be marked for each series of tomographic images. When a marker is active (for example, during a marker key is pressed), paging may be always started from an image marked.

(5) Other Functions:

The device of this embodiment comprises an enlargement key 328 and a measurement key 329. The enlargement key may be used for enlarging or reducing a selected screen.

The measurement key 329 is a key for giving a command of measuring CT values (corresponding to brightness) within a selected range. For example, a scanning range is defined with the track ball 324 and the button 325 and the measurement key is pressed to display CT values on the display. The scanning range may be defined as a circle or as a polygon.

FIG. 9 shows a range 330 defined as a polygon where an average CT value within the defined range under each image. The size of the defined range may be varied; specifically, for a circular range its size may be varied by changing a radius with the button 325 while for a polygonal range its size may be varied by drawing a polygon with the track ball 324 and the button 325.

Operation for keys not explained in Embodiment 2 are as described in Embodiment 1, but it may be changed as appropriate as long as it may not deviate from the purpose of this invention.

<Embodiment 3>

Figure 10:
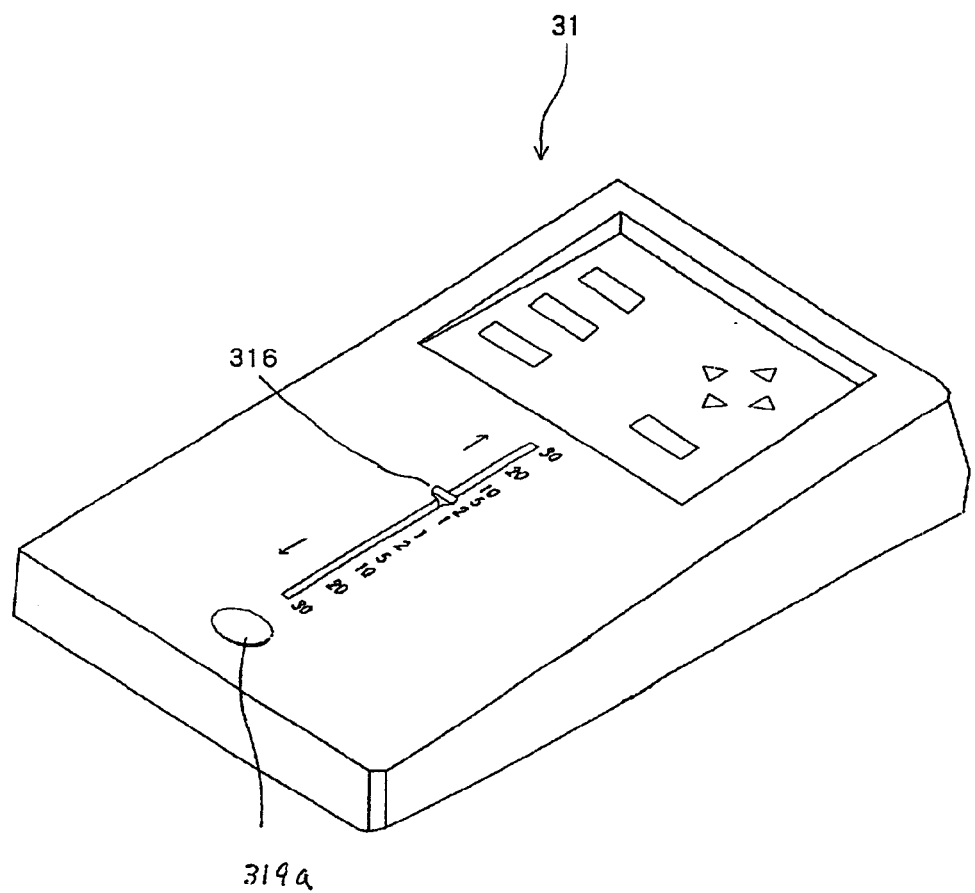
FIG. 10 shows an example of an operation unit.

In this embodiment, there will be described an example where an operation unit 31 comprising one mechanical slide bar 316 as illustrated in FIG. 10 may be used to realize relatively simple and intuitive operation without complicated functions.

There are the following features in display of a tomographic image according to this embodiment.

(1) DICOM Communication Function:

An image from X-ray CT or MRI is transferred to a controller portion via a network or storage mechanism such as DVD.

(2) Image Display Function:

Image data obtained are displayed on a display. For displaying, a single screen or two screens for comparison (for example, a simple CT and a contrasted CT) is selected.

(3) Image paging function:

Images are displayed in the manner of paging at a given speed. A display speed may be determined on the basis of a position of the mechanical slide bar 316 in the operation unit 31 in FIG. 10. For paging images with two-screen, only synchronized display is to be executable to achieve simple operation. However, two screens may be paged at different speeds if a user desires.

(4) Marker Function:

A starting point of paging images is set. This function may be used to mark an image to be examined. Marked images may be displayed in a matrix as described later.

(5) One-image Feeding/back-feeding Function:

Images displayed may be fed or back-fed one page in accordance with a trigger command. This function is possible during two-screen display for comparison.

(6) Enlargement Function:

A given part of an image may be enlarged. Furthermore, enlarged images may be displayed in the manner of paging.

(7) Matrix Display Function:

In default setting, several pieces before and after an interested image to be examined are displayed in the form of, e.g., 2×2 pieces (or 4×4 pieces). Alternatively, images marked by the marking function may be displayed as a matrix.

(8) Remote Control Function:

Operation such as start or stop of paging may be controlled via wired or wireless (e.g., infrared) communication from the operation unit. In this embodiment, start and stop are controlled with the key 319a in FIG. 10.

(9) Recording/Calling Function:

A required image is called and displayed on a display. A required image is stored in a storage unit in a computer.

The additional functions described in the above embodiments are not exclusively used for the individual embodiments described, but may be optionally applied to a display device for tomographic image of this invention if necessary.

Furthermore, the device of this invention may optionally have function displaying, for example, an image or values required for diagnosis as necessary. Examples of such function may be as follows.

(1) MPR (Multi Planar Reconstruction) Formation:

This is a function that a plurality of cross sections are displayed in one screen. For example, an axial, a suggital and a coronal cross sections may be displayed.

(2) Matrix Displaying:

As already described in the embodiments, target images are simultaneously aligned. This function may be used in place of a Schaukasten of the prior art.

(3) MIP (Maximum Intensity Projection) Image:

Data obtained from multislicing and helical scanning are projected to one direction and data with the highest CT value in each pixel are imaged.

(4) Averaged Image Displaying:

This function displays an averaged image of scanning data for several pieces. Pictures taken with a fine pitch may provide so enormous amount of scanning data, leading to a longer time for image reading. In this case, information for an abnormal site such as a tumor is certainly included in the image data even after averaging. Therefore, after observing the averaged image, an area around a site where abnormality is suspected may be displayed again in a fine pitch.

(5) Indicating CT Values For A Displayed Image:

In an X-ray CT image, each dot has an inherent CT value (bone: 1000, water: 0, air: -1000) based on a tissue at the site. Thus, a CT value displayed may be specified with a central CT value (WL) and a CT value width (WW) to display a desired particular tissue.

Figure 11:
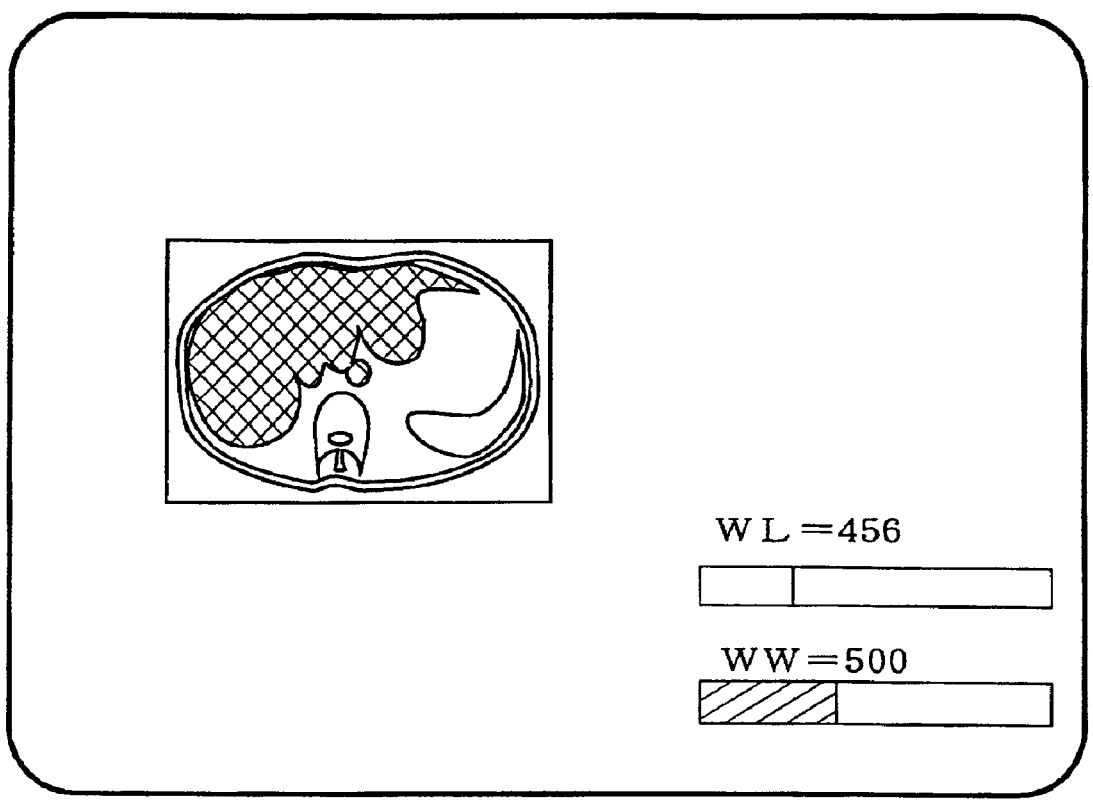
FIG. 11 illustrates a method for indicating CT values according to the prior art.
Figure 12:
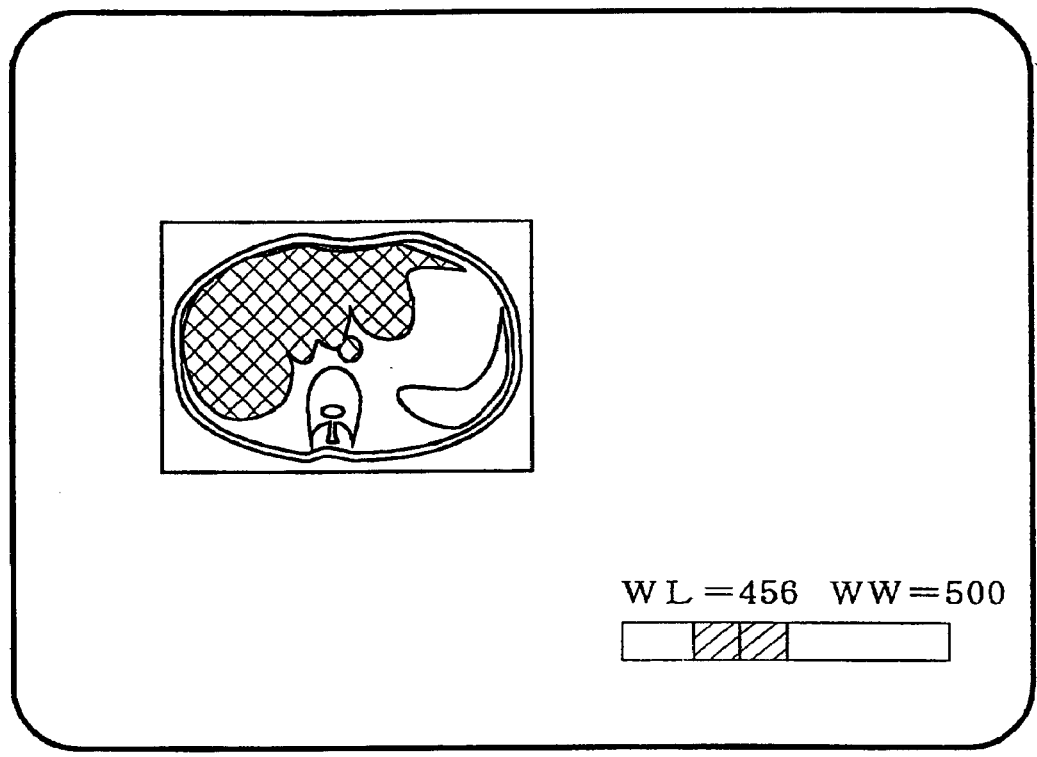
FIG. 12 illustrates a method for indicating CT values according to this invention.
Figure 13:
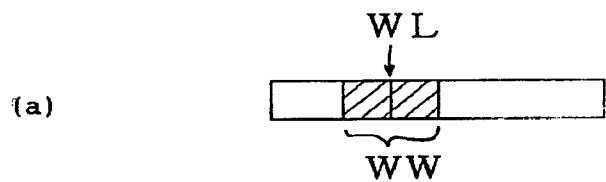
FIG. 13 illustrates a method for indicating CT values according to this invention.
Figure 13:
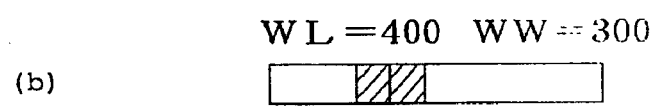
Figure 13:
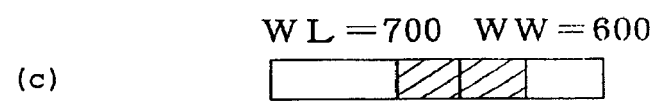

Range of CT value for a displayed image may be indicated on a display device by conventionally indicating a central CT value (WL) and a CT value width (WW) with one bar as shown in FIG. 11. However, indicating the central CT value (WL) and the CT value width (WW) with one bar is considerably convenient as shown in FIG. 12 because one can intuitively understand the displayed range. FIG. 13 is an enlarged view of the indicating bar. In this example, the center is indicated with a bold line (or may be highlighted with a different color) and the width is indicated with a given color distinctive from background color. FIGS. 13 (b) and (c) show the cases of WL=400, WW=300 and WL=700, WW=600, respectively.

To accomplish these functions, in accordance with program, a computer as a controller sends a command to locate and reserve area in the form of a bar on the display. As explained above, the bar may be a rectangular shape and each end of the bar defines a minimum value and a maximum value of necessary display range of CT value. As minimum value and maximum value -1000 and 1000 may used, respectively. Alternatively, these may be set for necessary range for diagnosis.

Usually, the display device may also comprise a receiving portion for receiving a CT value range to be displayed. The receiving portion preferably comprises two knobs where one is used for setting the center value and another is used for setting the width, thereby, the range of CT values to be displayed is defined. Then, the received CT value range is allocated in the display area in the form of bar. The range of CT values is expressed by the distinctive color from that of the display area as CT value width. The center of the range is expressed by further visibly distinctive color or shape.

Such an indication method of CT values is suitably used in a display device for tomographic image of this invention capable of displaying images in the manner of paging, but may be also used in a conventional display device for tomographic image without such a function.

In the above description, this invention has been described mainly in relation to an X-ray CT image, but this invention may be used as a display device for a two-dimensional tomographic image such as an MRI image, an angio-image and an angiographic image.

As described above, this invention can provide a display device for a tomographic image which is convenient and of good operability for paging at least two series of tomographic images and thus can provide a display device for a tomographic image allowing us to conduct more reliable diagnosis.

What is claimed is:

1. A display device for tomographic image, comprising:
    a display portion configured to display at least one series of tomographic images;
    a storage mechanism configured to store at least one series of tomographic image data;
    a display-speed setting mechanism setting configured to set a display speed for said at least one series of tomographic images; and
    a controller configured to receive data from the storage mechanism for displaying the at least one series of tomographic images by paging on the display portion based on the display speed set by the display-speed setting mechanism, wherein
    the display-speed setting mechanism is a mechanical slide-bar variable adjuster positioned in a separate case from that a case comprising the controller.

2. A display device for tomographic image, comprising:
    a display portion configured to display at least two series of tomographic images;
    a storage mechanism configured to store at least two series of tomographic image data;
    a display-speed setting mechanism configured to set display speeds of each series for the at least two series of tomographic images;
    a controller configured to receive data from the storage mechanism for each series and simultaneously displays the at least two series of tomographic images on the display portion based on the speed the display speeds set by the display-speed setting mechanism; and
    a synchronization command sending mechanism configured to match the display speeds for the at least two series of tomographic images, wherein
    the controller displays tomographic images of the at least two series by paging while synchronizing the display speeds for the at least two series of tomographic images based on a synchronizing command from the synchronization command sending mechanism, and
    the at least two series displayed comprise a first series obtained using a contrast medium and a second series obtained without a contrast medium for a same portion of a body and the first and second series are obtained during a same diagnostic time.

3. The display device for tomographic image as claimed in claim 2, wherein the display-speed setting mechanism is a mechanical variable adjusting knob in a separate case from a case comprising the controller.

4. The display device for tomographic image as claimed in claim 3, wherein the mechanical variable adjusting knob is a mechanical slide-bar type of variable adjuster.

5. The display device for tomographic image as claimed in claim 2, wherein the display-speed setting mechanism is a keyboard or a mouse that based on software sets the display speeds.

6. The display device for tomographic image as claimed in claim 2, further comprising a receiving portion configured to receive a CT value range to be displayed on the image display portion, wherein the display device is adapted to accomplish the method comprising the steps of:

locating a display area in the form of a bar whose ends define a minimum value and a maximum value of a necessary display range of a CT value;

receiving the CT value range to be displayed on the image display portion;

indicating the received CT value range on the display area using visibly distinctive color;

indicating a center of the received CT value range using further visibly distinctive color or shape; and showing CT values currently displayed on said image display portion.

7. A display device for tomographic image, comprising:

a display portion configured to display at least two series of tomographic images;

a storage mechanism configured to store at least two series of tomographic image data;

a display-speed setting mechanism configured to set display speeds of each series for the at least two series of tomographic images;

a controller configured to receive data from the storage mechanism for each series and simultaneously displays the at least two series of tomographic images on the display portion based on the display speeds set by the display-speed setting mechanism; and a synchronization command sending mechanism configured to match the display speeds for the at least two series of tomographic images when a number of image in each of the at least two series is different, wherein the controller displays tomographic images by paging while synchronizing the display speeds for the at least two series of tomographic images based on a synchronization command from the synchronization command sending mechanism.

* * * * *